United States Patent [19]

Miyajima

[11] Patent Number: 5,441,052

[45] Date of Patent: Aug. 15, 1995

[54] COLOR DOPPLER-TYPE ULTRASONIC DIAGNOSTIC APPARATUS

[75] Inventor: Yasuo Miyajima, Utsunomiya, Japan

[73] Assignee: Kabushiki Kaisha Toshiba, Kanagawa, Japan

[21] Appl. No.: 173,115

[22] Filed: Dec. 27, 1993

[30] Foreign Application Priority Data

Dec. 28, 1992 [JP] Japan .................... 4-349066

[51] Int. Cl.⁶ .................................................. A61B 8/00
[52] U.S. Cl. ............................................ 128/661.09
[58] Field of Search .................... 128/661.08, 661.09, 128/661.10, 660.07, 660.05, 660.04, 661.01

[56] References Cited

U.S. PATENT DOCUMENTS

| | | | |
|---|---|---|---|
| 5,188,113 | 2/1993 | Sato et al. | 128/661.09 |
| 5,211,169 | 5/1993 | Freeland | 128/661.10 |
| 5,282,471 | 2/1994 | Sato | 128/661.09 |

FOREIGN PATENT DOCUMENTS 61-206433 9/1986 Japan .
5-31110 7/1991 Japan .

*Primary Examiner*—George Manuel
*Attorney, Agent, or Firm*—Finnegan, Henderson, Farabow, Garrett & Dunner

[57] ABSTRACT

A color Doppler-type ultrasonic apparatus is provided in which an ultrasonic pulse beam is transmitted, from a transducer, along a tomographic plane to be scanned toward an object containing a moving target. A Doppler shift frequency is detected on the basis of an echoed ultrasonic pulse beam for every sampling volume of the tomographic plane, and an image of the tomographic plane is displayed. The apparatus comprises an element for calculating movement information including a direction and a magnitude of velocity of the moving target for each of the sampling volumes on the basis of the detected Doppler shift frequency, an element for specifying a reference direction on the image of the tomographic plane, an element for forming data of a color sample showing a directional relation between the calculated directions and the reference direction, an element for creating data for color display of the calculated velocity for each of the sampling volumes on the basis of the directional relation; and an element for color-displaying at least the created data for color display together with the formed data of color sample.

47 Claims, 16 Drawing Sheets

{ REF. DIRECTION: -160°  
BEAM DIRECTION (CENTER): -110°C  
DISPLAY COLOR OF REF. DIRECTION  
: BLUE OR THE LIKE }

| (a) CALCULATED BLOOD FLOW DIRECTION [VALUE INSIDE PARENTHESES IS ANGLE BETWEEN BLOOD FLOW DIRECTION AND BEAM DIRECTION] | (b) DIFFERENCE FROM REF. DIRECTION | (c) CODE FOR CONVERSION | (d) DISPLAY COLOR |
|---|---|---|---|
| 0° ( 110° ) | 160° | 16 | RED$^x$ |
| 10° ( 120° ) | 170° | 17 | RED$^x$ |
| 20° ( 130° ) | 180° | 18 | RED$^x$ |
| 30° ( 140° ) | -170° | -17 | RED$^x$ |
| 40° ( 150° ) | -160° | -16 | RED$^x$ |
| 50° ( 160° ) | -150° | -15 | RED$^x$ |
| 60° ( 170° ) | -140° | -14 | RED$^x$ |
| 70° ( 180° ) | -130° | -13 | RED$^x$ |
| 80° (-170° ) | -120° | -12 | RED$^x$ |
| 90° (-160° ) | -110° | -11 | RED$^x$ |
| 100° (-150° ) | -100° | -10 | RED$^x$ |
| 110° (-140° ) | -90° | -9 | BLUE$^x$ |
| 120° (-130° ) | -80° | -8 | BLUE$^x$ |
| 130° (-120° ) | -70° | -7 | BLUE$^x$ |
| 140° (-110° ) | -60° | -6 | BLUE$^x$ |
| 150° (-100° ) | POOR ACCURACY | 99 | VIOLET |
| 160° ( -90° ) | POOR ACCURACY | 99 | VIOLET |
| 170° ( -80° ) | POOR ACCURACY | 99 | VIOLET |
| 180° ( -70° ) | -20° | -2 | BLUE$^x$ |
| -170° ( -60° ) | -10° | -1 | BLUE$^x$ |
| -160° ( -50° ) | 0° | 0 | BLUE$^x$ |
| -150° ( -40° ) | 10° | 1 | BLUE$^x$ |
| -140° ( -30° ) | 20° | 2 | BLUE$^x$ |
| -130° ( -20° ) | 30° | 3 | BLUE$^x$ |
| -120° ( -10° ) | 40° | 4 | BLUE$^x$ |
| -110° ( 0° ) | 50° | 5 | BLUE$^x$ |
| -100° ( 10° ) | 60° | 6 | BLUE$^x$ |
| -90° ( 20° ) | 70° | 7 | BLUE$^x$ |
| -80° ( 30° ) | 80° | 8 | BLUE$^x$ |
| -70° ( 40° ) | 90° | 9 | RED$^x$ |
| -60° ( 50° ) | 100° | 10 | RED$^x$ |
| -50° ( 60° ) | 110° | 11 | RED$^x$ |
| -40° ( 70° ) | 120° | 12 | RED$^x$ |
| -30° ( 80° ) | POOR ACCURACY | 99 | VIOLET |
| -20° ( 90° ) | POOR ACCURACY | 99 | VIOLET |
| -10° ( 100° ) | POOR ACCURACY | 99 | VIOLET |

{ RED$^x$: RED OR THE LIKE  
BLUE$^x$: BLUE OR THE LIKE }

FIG. 6

$$\begin{bmatrix} \text{REF. DIRECTION}: 0° \\ \text{BEAM DIRECTION (CENTER)}: -110°\text{C} \\ \text{DISPLAY COLOR OF REF. DIRECTION} \\ : \text{RED OR THE LIKE} \end{bmatrix}$$

| (a) CALCULATED BLOOD FLOW DIRECTION [VALUE INSIDE PARENTHESES IS ANGLE BETWEEN BLOOD FLOW DIRECTION AND BEAM DIRECTION] | (b) DIFFERENCE FROM REF. DIRECTION | (c) CODE FOR CONVERSION | (d) DISPLAY COLOR |
|---|---|---|---|
| 0° ( 110° ) | 0° | 0 | RED* |
| 10° ( 120° ) | 10° | 1 | RED* |
| 20° ( 130° ) | 20° | 2 | RED* |
| 30° ( 140° ) | 30° | 3 | RED* |
| 40° ( 150° ) | 40° | 4 | RED* |
| 50° ( 160° ) | 50° | 5 | RED* |
| 60° ( 170° ) | 60° | 6 | RED* |
| 70° ( 180° ) | 70° | 7 | RED* |
| 80° (−170° ) | 80° | 8 | RED* |
| 90° (−160° ) | 90° | 9 | RED* |
| 100° (−150° ) | 100° | 10 | BLUE* |
| 110° (−140° ) | 110° | 11 | BLUE* |
| 120° (−130° ) | 120° | 12 | BLUE* |
| 130° (−120° ) | 130° | 13 | BLUE* |
| 140° (−110° ) | 140° | 14 | BLUE* |
| 150° (−100° ) | POOR ACCURACY | 99 | VIOLET |
| 160° (− 90° ) | POOR ACCURACY | 99 | VIOLET |
| 170° (− 80° ) | POOR ACCURACY | 99 | VIOLET |
| 180° (− 70° ) | 180° | 18 | BLUE* |
| −170° (− 60° ) | −170° | −17 | BLUE* |
| −160° (− 50° ) | −160° | −16 | BLUE* |
| −150° (− 40° ) | −150° | −15 | BLUE* |
| −140° (− 30° ) | −140° | −14 | BLUE* |
| −130° (− 20° ) | −130° | −13 | BLUE* |
| −120° (− 10° ) | −120° | −12 | BLUE* |
| −110° ( 0° ) | −110° | −11 | BLUE* |
| −100° ( 10° ) | −100° | −10 | BLUE* |
| − 90° ( 20° ) | − 90° | − 9 | BLUE* |
| − 80° ( 30° ) | − 80° | − 8 | RED* |
| − 70° ( 40° ) | − 70° | − 7 | RED* |
| − 60° ( 50° ) | − 60° | − 6 | RED* |
| − 50° ( 60° ) | − 50° | − 5 | RED* |
| − 40° ( 70° ) | − 40° | − 4 | RED* |
| − 30° ( 80° ) | POOR ACCURACY | 99 | VIOLET |
| − 20° ( 90° ) | POOR ACCURACY | 99 | VIOLET |
| − 10° ( 100° ) | POOR ACCURACY | 99 | VIOLET |

$$\begin{bmatrix} \text{RED* : RED OR THE LIKE} \\ \text{BLUE* : BLUE OR THE LIKE} \end{bmatrix}$$

FIG. 7

COLOR DOPPLER-TYPE ULTRASONIC DIAGNOSTIC APPARATUS

BACKGROUND OF THE INVENTION

The present invention relates to a color Doppler-type ultrasonic diagnostic apparatus which displays in color a distribution image of movement information for fluid, such as a flow of blood flowing in an object to be examined, or for a cardiac muscle of a heart, and in particular, to an improvement for display on a monitor of the apparatus.

A color Doppler-type ultrasonic diagnostic apparatus functions by detecting frequency shifts, caused by the Doppler effect of ultrasonic pulses transmitted toward an object being examined by means of frequency analysis of received echo signals, and displaying a distribution image of a flow of blood based on the detected results.

The detectable frequency shift (hereinafter, referred to as a Doppler shift component) in this apparatus corresponds to a component of velocity in an ultrasonic beam direction. For instance, as shown in FIG. 1, an ultrasonic beam is transmitted from an ultrasonic probe PB to a flow of blood BD in motion at a velocity of V. If $\theta$ is provided as an angle between the movement direction of the blood flow and the ultrasonic beam direction, the Doppler shift component, that is, the detectable velocity Va can be expressed as follows.

$$Va = V \cdot \cos \theta$$

As is apparent from this expression, when the blood flow is in motion along the axis of the ultrasonic beam (i.e. the angle $\theta = 0$), the maximum Doppler shift component is obtained, leading to highly accurate measurement of velocity of the blood flow. On the other hand, deviation of the blood flow direction from the ultrasonic beam direction will cause the Doppler shift component to reduce by a value of "V−va" resulting from the angle $\theta$, thereby deteriorating measurement accuracy.

In order to avoid the problem of the angle $\theta$ when obtaining an absolute velocity of a blood flow (in this invention, "an absolute velocity" means "a velocity of a blood flow in its flowing direction itself" having its direction and magnitude as a vector value), there are several automatic correction methods. One of the correction methods obtains Doppler signals in two directions set apart by a small angle of $\Delta\theta$ for an observing point and calculates an absolute velocity V. In another method a plurality of groups of piezoelectric transducers formed on a single probe are driven, through electric scanning, to obtain a plurality of Doppler signals by transmitting/receiving a plurality of ultrasonic beams along different directions to the same observing point, and the plural Doppler signals are used for an absolute velocity V.

In conventional display for corrected vector information of an absolute velocity of a blood flow, there is a widely known display method; a blood flow coming near a probe is shown in red or the like and a blood flow going away from the probe is shown in blue or the like.

During the diagnosis of abnormalities of blood flows, information which indicates whether a blood flow is in a direction away from a central portion, such as a heart, toward a peripheral portion, or in the opposite direction, is a matter of great importance.

However, blood vessels, including superficial blood vessels which run parallel to the body surface provide approximately parallel flows to the body surface and are thus approximately perpendicular to the ultrasonic beam. Accordingly, in the conventional color display (i.e., a display which selects either one of red or the like or blue or the like), the direction of the probe (i.e. the ultrasonic beam direction) affects largely the detection results of the blood flow.

In particular, a slight change in the beam direction to the blood flow causes the blood flow direction to fluctuate sensitively between the two directions of approaching the probe and going away from it. As the beam direction is frequently changed by operator handling of adjustment of a scanning angle in a linear scanning, such sensitive fluctuation requires the operator to pay excessive attention to the beam direction, creating much operation work.

In sector and convex scannings, the changes in the beam direction cause the displayed color on the same image to be changed between red and blue for even the same blood vessel. This makes it difficult to clearly recognize the directions of blood vessels on the image displayed. Namely, it is not easy to understand at a glance whether the direction of a blood flow is in a direction flowing away from a central portion (e.g. heart) toward a peripheral portion (e.g. internal organs) or in an opposite direction. In this case, an operator is required to adjust the ultrasonic beam direction or estimate the blood flow direction of an image shown by a monitor by using the operator's experience. This becomes an excessive operation.

Of course, while ignoring such excessive operation work or trouble resulting from changes in the beam direction, it is possible to color-display only the absolute values of blood flow velocities, without displaying the directions of the flows. But this is insufficient information for diagnosis, because flow directions aid in determining normal or abnormal directions of flows.

There is a further problem in the above mentioned conventional apparatus. In an image of a distribution of blood flows overlapped on a tomographic image, it is easy to estimate the direction of a blood flow when the blood vessel runs through the tomographic image over a long distance. However, if a blood vessel is across the tomographic image (plane), it is very difficult to consider the crossing angle therebetween and measure the direction of a blood flow. In such a case, two cross sections are necessary to be examined.

SUMMARY OF THE INVENTION

Accordingly, it is a primary object of the present invention to provide a color Doppler-type ultrasonic diagnostic apparatus that displays a color distribution image of fluids, such as blood flows, representing their movement directions with high accuracy and sufficient ease.

It is a further object of the present invention to prevent the displayed color of the same blood vessel from being fluctuated, even when the angle of a probe to the body surface and/or directions of ultrasonic beams are changed.

It is a further object of the present invention to provide the above color distribution image in which the movement direction and the absolute value of a velocity of a fluid can be displayed at the same time.

It is a still further object of the present invention to provide a color Doppler-type ultrasonic diagnostic apparatus that is properly applicable to a linear, sector, and convex scannings and obtain a color distribution image of fluids representing their movement directions with high accuracy and sufficient ease.

It is a still further object of the present invention to display, together with a color distribution image, additional information including detectable minimum and maximum velocities for each direction of the blood flows.

These and other objects can be achieved according to the present invention, in one aspect by providing, a color Doppler-type ultrasonic diagnostic apparatus in which an ultrasonic pulse beam is transmitted from a transducer along a tomographic plane to be scanned toward an object being examined and containing a moving target therein, a Doppler shift frequency is detected on the basis of an echoed ultrasonic pulse beam from the moving target for every sampling volume of the tomographic plane, and an image of the tomographic plane is displayed, the apparatus comprising: means for calculating movement information including a direction and a magnitude of velocity of the moving target for each of the sampling volumes on the basis of the detected Doppler shift frequency; means for specifying a reference direction on the image of the tomographic plane; means for forming data of a color sample showing a directional relation between the calculated directions and the reference direction; means for creating data for color display of the calculated velocity for each of the sampling volumes on the basis of the directional relation; and means for color-displaying at least the created data for color display together with the formed data of color sample.

Preferably, the moving target is a flow of blood.

It is preferred that the ultrasonic beams are scanned by electronic linear scanning in which a scanning angle of the ultrasonic pulse beam is unchanged over its scanning lines.

It is also preferred that the specifying means comprises means capable of being pointed at a desired reference position on the tomographic plane; and means for setting the reference direction at the reference position using the calculated direction at the reference position.

Accordingly, the distribution image of the moving target is displayed together with the color sample. On the distribution image, for every sampling volume, the movement direction along the reference direction is colored in blue and the movement direction against the reference direction in red, for instance. Therefore, if the reference direction is specified as a flow direction at a cervical vein, all the cervical veins are displayed in blue on the image and all the carotid arteries that have opposite flow to the veins are displayed in red. In particular, where the cervical vein and carotid artery have branches, the displayed colors are not changed unless they flow in reverse. Hence, when a superficial blood vessel is examined, the examination is not affected by changes in scanning angles of an ultrasonic beam, thereby blood vessels are examined easily and accurately.

BRIEF DESCRIPTION OF THE DRAWINGS

The accompanying drawings which are incorporated in and constitute a part of this specification, illustrate embodiments of the present invention and, together with the description, serve to explain the principles of the present invention. In the drawings:

FIG. 6 is an example of a table data representing code and color conversions of blood flow directions;

FIG. 7 is another example of a table data representing code and color conversions of blood flow directions;

DESCRIPTION OF THE PREFERRED EMBODIMENTS

A first embodiment of the present invention will now be described according to FIGS. 2 to 8.

Figure 1:
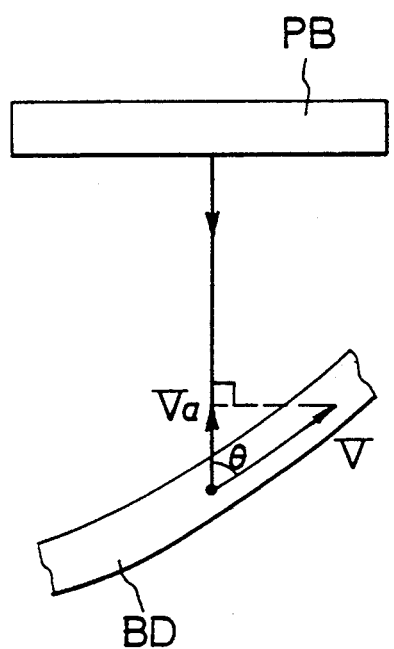
FIG. 1 is a pictorial illustration showing the direction of a ultrasonic beam and the direction of a blood flow.
Figure 2:
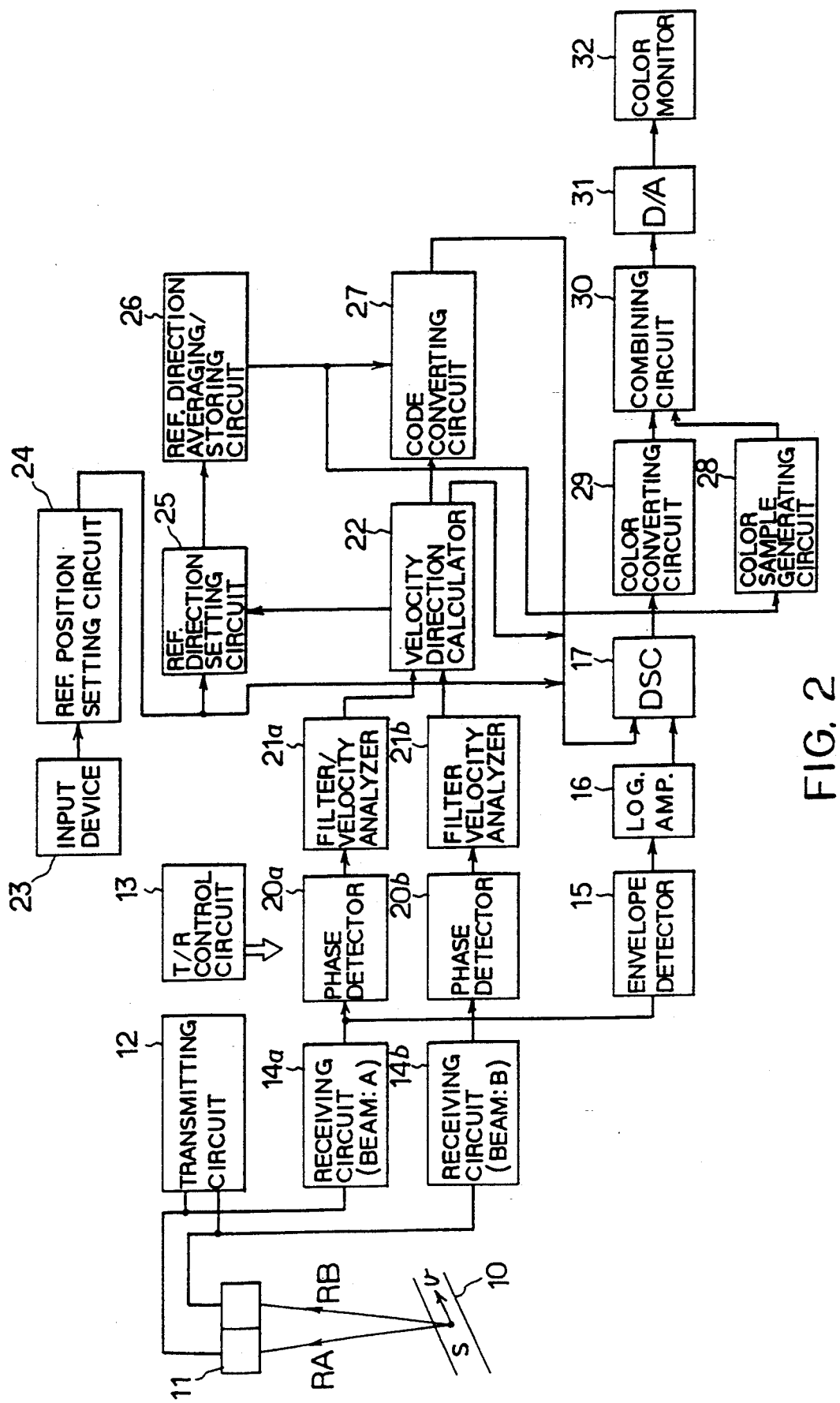
FIG. 2 shows in block form a first example of a color Doppler-type ultrasonic diagnostic apparatus according to the present invention.

FIG. 2 is a block diagram schematically representing the whole construction of a color Doppler-type ultrasonic diagnostic apparatus of the first embodiment.

The ultrasonic diagnostic apparatus shown therein comprises a piezoelectric transducer 11 for transmitting ultrasonic pulses toward a blood vessel as an object being examined, and receiving their echo pulses. The transducer 11 is incorporated in an ultrasonic probe and formed into an array-type structure in which a plurality of vibrators are aligned linearly in a scanning direction. These vibrators are connected to a transmitting circuit 12, which drives the vibrators when receiving an instruction of transmission from a transmitting/receiving control circuit 13. Such activation permits each of the vibrators to transmit ultrasonic pulses toward a diagnostic portion including the desired blood vessel 10.

The transmitted ultrasonic pulses will then reflect at the diagnostic portion and form echo pulses. The echo pulses are received by the vibrators and converted into corresponding voltage signals. For this reception of the echo pulses, signal processing will be done so that the whole transducer 11 forms two divided reception apertures. Each half of the vibrators, which belong to each of the two apertures, is connected with a receiving circuit 14a or 14b.

Each of the receiving circuits 14a and 14b has preamplifiers and delay lines connected with specified vibrators and an adder adding outputs from the delay lines. Delay times of the delay lines are specified by an instruction from the transmitting/receiving control circuit 13. Thus, controlling a pattern of the delay times enables the receiving circuits 14a and 14b to form receiving ultrasonic beams, at every aperture, for focusing on a position of sampling volume being observed. Such beam forming may be achieved by a time sharing method, where a single receiving circuit is used.

The output of one receiving circuit 14a is connected through an envelope detector 15 and a logarithmic amplifier 16, with one of two inputs of a digital scan converter (DSC) 17. Accordingly, tomographic data of a B-mode (and data of an M-mode, if required) are obtained and supplied to the DSC 17.

Further, the outputs of the receiving circuits 14a and 14b are connected, via phase detectors 20a and 20b, with filter/velocity analyzer 21a and 21b, respectively. Therefore, the signals of the receiving ultrasonic beams formed by the receiving circuit 14a and 14b will be each phase-detected at the phase detector 20a and 20b. These detected signals are not only filtered for removal of clutter but processed for their velocity analysis at the filter/velocity analyzer 21a and 21b. In detail, in the velocity analysis, Fourier transform is used to calculate Doppler shift frequencies in directions of receiving ultrasonic beams. The Doppler shift frequencies correspond to velocity components of blood flows in the receiving ultrasonic beam directions.

The outputs of the filter/velocity analyzer 21a and 21b are then supplied to a velocity/direction calculator 22. The calculator 22 calculates a velocity ("absolute velocity", in this sense) of a blood flow, using the following calculation method.

Figure 3:
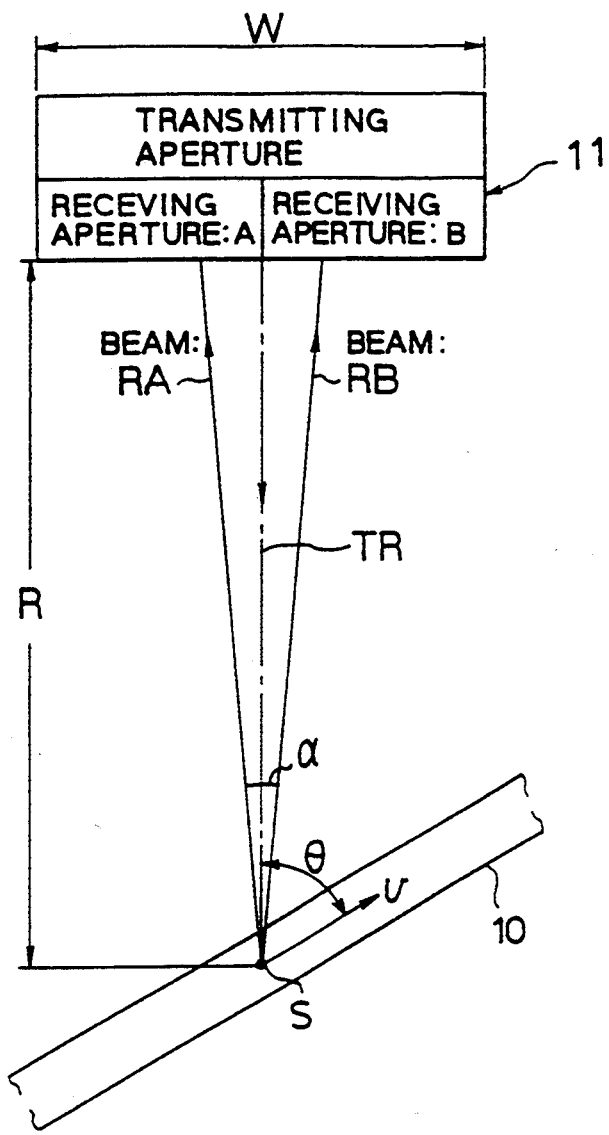
FIG. 3 is a pictorial illustration showing a principle of detecting the direction and velocity of a blood flow in this invention.

Now, a simplified situation will be introduced as shown in FIG. 3. In the configuration of FIG. 3, a sampling volume S is positioned in front of the transducer 11 and two receiving ultrasonic beams RA and RB are delay-controlled so that they are focused on the same sampling volume (detecting position) S from their individual receiving apertures A and B. In this situation, as explained above, the filter/velocity analyzers 21a and 21b output Doppler shift frequencies $f_A$ and $f_B$ in the directions of the receiving ultrasonic beam RA and RB. The frequencies $f_A$ and $f_B$ are expressed as follows:

$$f_A = \frac{f_0 \cdot v}{c} \left[ \cos\theta + \cos\left(\theta + \tan^{-1}\left(\frac{W}{4R}\right)\right) \right] \quad (1)$$

$$f_B = \frac{f_0 \cdot v}{c} \left[ \cos\theta + \cos\left(\theta - \tan^{-1}\left(\frac{W}{4R}\right)\right) \right] \quad (2)$$

, where $f_0$ is a transmitting frequency of ultrasonic pulses, v is an absolute velocity of a reflector (blood flow) at the sampling volume position, c is a sound speed in a medium, $\theta$ is an angle between the directions of the transmitting ultrasonic beam and the blood flow, W is a length of the transmitting aperture of the transducer, and R is a distance between the transducer and the sampling volume position.

In the above expressions (1) and (2), $f_A$ and $f_B$ are values calculated by the analyzer 21a and 21b and $f_0$, c, W and R are known values. Thus, from the expressions (1) and (2), the angle $\theta$ is obtained below:

$$\theta = \tan^{-1}\left\{ \frac{f_B - f_A}{f_B + f_A} \times \frac{(1 + (W/4R)^2)^{\frac{1}{2}} + 1}{(W/4R)} \right\} \quad (3)$$

Substituting the expression (3) for $\theta$ in the expression (1) produces the following expression (4) which represents the absolute velocity v of the blood flow.

$$v = \frac{f_A \cdot c}{f_0} \left\{ \cos\left[ \tan^{-1}\left\{ \frac{f_B - f_A}{f_A + f_B} \times \frac{(1 + (W/4R)^2)^{\frac{1}{2}} + 1}{(W/4R)} \right\} \right] + \cos\left[ \tan^{-1}\left\{ \frac{f_B - f_A}{f_A + f_B} \times \frac{(1 + (W/4R)^2)^{\frac{1}{2}} + 1}{(W/4R)} \right\} + \tan^{-1}(W/4R) \right] \right\} \quad (4)$$

The aforementioned velocity/direction calculator 22 calculates a vector velocity (v, $\theta$) - that is, absolute velocity, of a blood flow on the basis of the expression (3) and (4). The direction and magnitude of a blood flow correspond to the direction and magnitude of an absolute velocity.

Furthermore, in the ultrasonic diagnostic apparatus of the embodiment, there are a wide variety of circuits for designating a blood flow direction as a reference direction at a reference position (the term "position" here includes the concept of "a region") and color-displaying the absolute velocities (vector values) of blood flows by relating all of the calculation results of the velocity/direction calculator 22 to the reference direction. Among such circuits are an input device 23, reference position setting circuit 24, reference direction setting circuit 25, converting circuit 27, and color sample generating circuit 28.

The input device 23, operated by an operator, is a key board or a track ball, for instance.

The reference position setting circuit 24 is for setting a desired reference position on a tomographic image displayed by a monitor on the basis of an instruction from the input device 23. The data of the set reference position is supplied to the other of the two inputs of the DSC 17 and displayed in real time on a color monitor 32 (as described below), for example, as a rectangular region of interest (ROI). Therefore, the operator may being the reference position to a desired location by observing the screen of the color monitor 32.

The data of the reference position is also provided to the reference direction setting circuit 25. The reference direction setting circuit 25 also receives direction data of velocities (i.e. data of blood flow directions) supplied from the velocity/direction calculator 22. The reference direction setting circuit 25 calculates an averaged direction as a reference direction at the reference position (or area) at a time; for example, the circuit 25 averages an autocorrelation function at the reference position or averages vector direction data within the reference position (or area).

The signal of the reference direction is sent to the reference direction averaging/storing circuit 26, in which the reference direction is averaged over a certain period of time and the value of the averaged direction is then stored temporarily therein. The time-averaged direction data are then sent to the code converting circuit 27 and color sample generating circuit 28. From the velocity/direction calculator 22, the data of directions of velocities (absolute velocities) are supplied to the code converting circuit 27, and the data of magnitudes of velocities (absolute velocities) are supplied to the DSC 17.

The code converting circuit 27 compares, for every sampling volume, the detected directions (blood flow directions) with the reference direction to produce relative direction data which are then sent to both of the DSC 17 and color sample generating circuit 28.

Now the above mentioned code conversion will be explained in detail.

Figure 4:
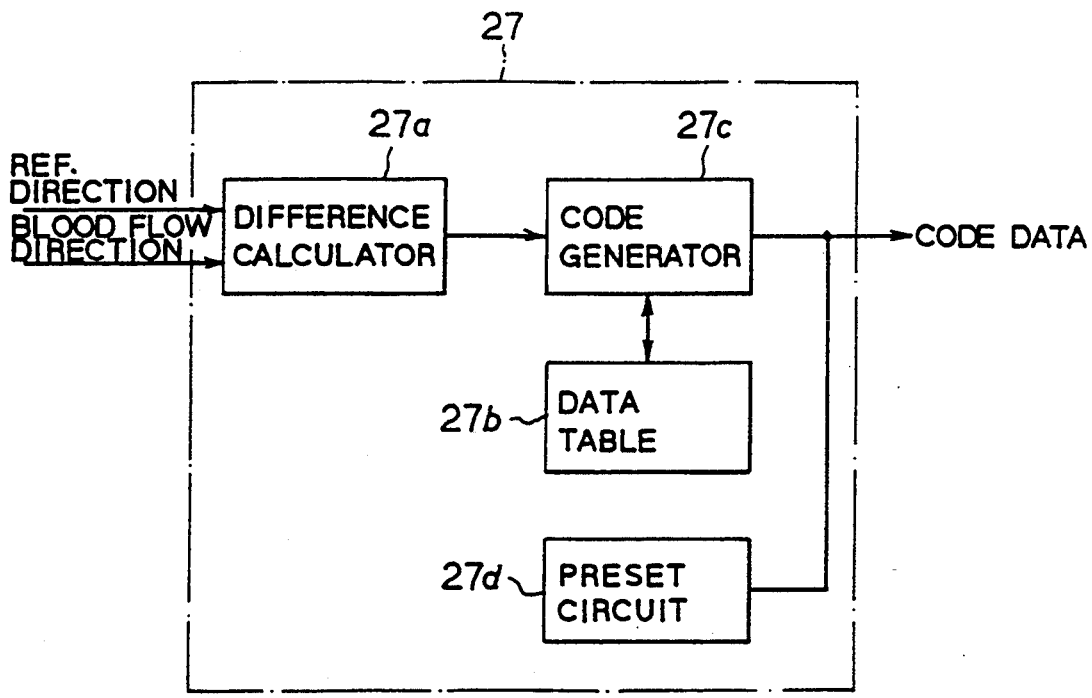
FIG. 4 shows in block form a code converting circuit of the apparatus.

The code converting circuit 27, as shown in FIG. 4, comprises a difference calculator 27a, a data table 27b, a code generator 27c, and a preset circuit 27d. The difference calculator 27a calculates, for every sampling volume, a difference in angle between a given reference direction (angle data) and detected blood flow directions (angle data). The calculated difference data are sent to the code generator 27c, in which the difference data are converted into corresponding codes for every sampling volume by referring to the data table 27b. The data table 27b prestores data partly shown in FIG. 6. Namely, the data table 27b prestores data of columns (b) and (c) shown in FIG. 6, corresponding one by one to each other. The preset circuit 27d prestores information specifying a display color of the reference direction. In this embodiment, either blue or red can be selected. Blue is an arbitrary color among blue or the like, red is an arbitrary color among red or the like, and their brightness is constant.

Figure 5:
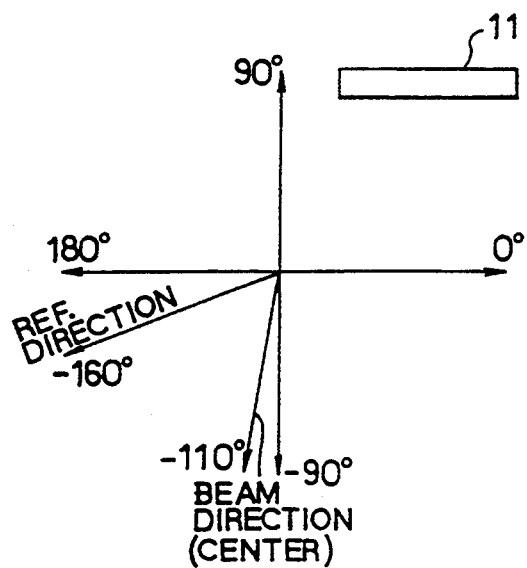
FIG. 5 shows a coordinate system set for a probe, in which a reference direction and an ultrasonic beam direction are illustrated.

One practical example is described below. As shown in FIG. 5, a coordinate system is depicted such that, an axis of zero degrees is parallel to the transmitting-/receiving surface of the traducer 11, an angle range down to −180 degrees is set clockwise and another angle range up to +180 degrees is set counterclockwise. Suppose that a reference direction is giver at −160 degrees and a center direction of receiving ultrasonic beams is given at −110 degrees. Further suppose that the reference direction is preset to be displayed in blue.

Accordingly, as shown in column (a) of FIG. 6, if the detected directions of blood flows lie within ranges of 0 to +180 degrees and −170 to −10 degrees, there are, as shown in column (b) of FIG. 6, differences from the reference direction (−160 degrees). In FIG. 6, when a detected blood flow direction lies within ranges of +150 to +170 degrees and −30 to −10 degrees, that is, a blood flow direction is almost perpendicular to either one of the two receiving ultrasonic beams (in this embodiment, "almost perpendicular" means a range of ±10 degrees from 90 degrees to the center line of the two receiving ultrasonic beams), the difference between the two directions will not be calculated, because of poor accuracy of measurement.

The data of difference in directions are then converted into conversion codes by the code generator 27c as follows. For example, if a detected blood flow direction is the same as the reference direction (−160 degree), that is, the direction difference is zero, the conversion code is "0" as shown in columns (b) and (c) of FIG. 6, if they differ by +180 degrees (i.e. the direction difference= +180 degrees), the conversion code is "+18", if they differ by +90 degrees (i.e. the direction difference= +90 degrees), the conversion code is "+9", and if they differ by −90 degrees (i.e. the direction difference= −90 degrees), the conversion code is "−9". Further, if a direction difference represents a condition of poor accuracy, the conversion code is a special "99".

The conversion data are defined, as shown in FIG. 6, every 10 degrees, but an arbitrary angle width can be selected.

The corrected code data of direction are supplied to the DSC 17. In the DSC 17, tomographic B-mode data and magnitude and direction data of blood flow velocities are converted from the ultrasonic scan to a standard TV scan and interpolated by a weighting process from neighboring pixel values, for example. The output of the DSC 17 is connected, through a color converting circuit 29, a combining circuit 30 and a D/A converter 31, to the color monitor 32.

For the code data which have been scan-converted and interpolated, the color converting circuit 29 determines colors of display by looking up a data table corresponding to a relation shown in columns (c) and (d) of FIG. 6. Thus, when the conversion code is "8 to −9", blue or the like is specified as the color of display. In contrast, when the conversion code is "9 to 18" and "−10 or less than −10", red or the like is specified as the color of display. In addition, when the conversion code is "99", violet is specified as the color of display. These specified colors are outputted as RGB video data from the color converting circuit 29. The RGB video data includes white/black data of B-mode tomographic data (or M-mode data).

Figure 8:
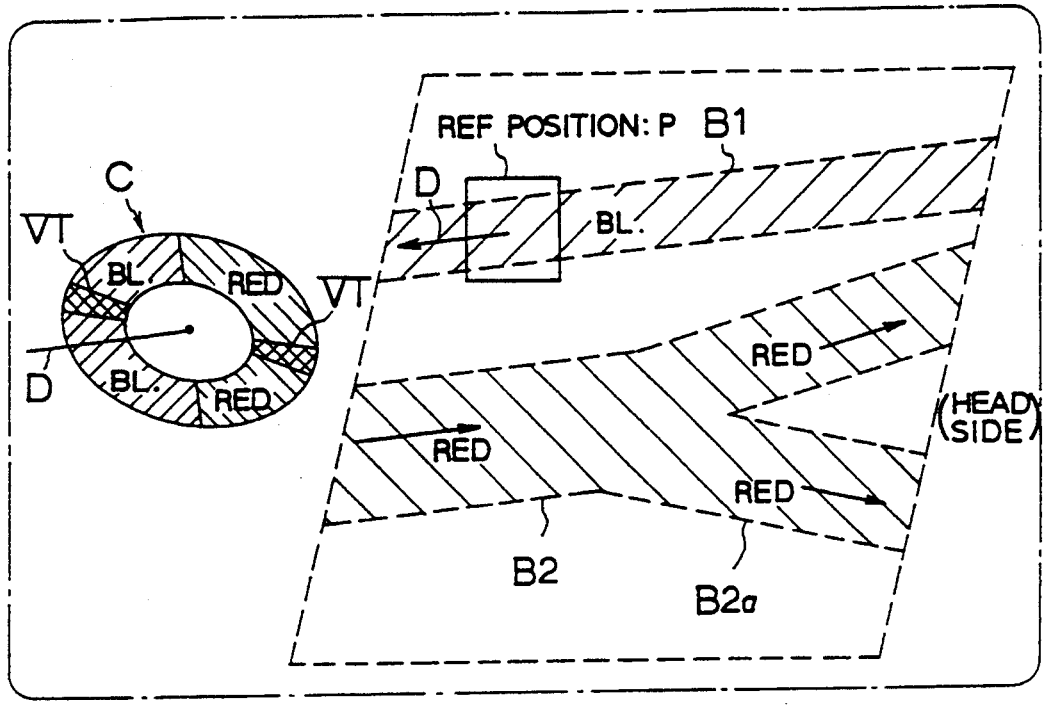
FIG. 8 is an example of a displayed image for a linear oblique scanning according to the first embodiment.

The color sample generating circuit 28 generates data of a ring-like color sample C shown in FIG. 8. The hues of the color sample C are defined by conversion based on a data table storing a relation between columns (b) and (d) of FIG. 6. Further, data of a marker having a shape of a vector, which corresponds to the reference direction D, is overlaid on the hue data. The display angle of the whole color sample C is set such that the direction represented by the marker is coincident with the reference direction D set on the monitor screen.

Then the RGB video data and data of the color sample is combined by the combining circuit 30, which is formed by a multiplexer, for instance. The combined data are then sent via the D/A converter 31 to the color monitor 32. As a result, the signals of the color sample having specified display colors are overlapped on the RGB video signals, color-converted and displayed in color on the monitor 32.

The data tables contained in the code converting circuit 27 and color converting circuit 29 are not limited to those shown in FIG. 6, and for example, the data tables shown in FIG. 7 can be used. The combination of conversion data shown in FIG. 7 is based on a condition in which the reference direction is zero degrees, the direction of the axial center of receiving ultrasonic beams is −110 degrees, and the display color of the reference direction is preset to be red.

In the present invention, a reference direction specifying means of the present invention is formed by the input device 23, reference position setting circuit 24, reference direction setting circuit 25, and reference direction averaging/storing circuit 26. A movement information calculating means is formed by receiving circuit 14a and 14b, phase detector 20a and 20b, filter/velocity analyzer 21a and 21b, and velocity/direction calculator 22. In addition, a display data creating means is formed by the code converting circuit 27, DSC 17, and color converting circuit 29. A color sample data forming means corresponds to the color converting circuit 29. A color displaying means of the invention is constructed by the combining circuit 30, D/A converter 31, and color monitor 32.

The entire operation of color Doppler imaging for blood flows will now be explained.

A positioning is performed so that the head of a patient is laid on the right-hand side of the screen of the monitor 32 as shown in FIG. 8, and a superficial blood vessel of the patient is linearly, obliquely scanned. The imaging color of the reference direction is preset to be blue and a certain value is given to the angle of the central axis of receiving ultrasonic beams.

In this situation, for instance, an operator manipulates the input device 23 to give a reference position data for a cervical vein B1 flowing toward the lower left side in the screen. This specification allows the reference position setting circuit 24 to designate a reference position (region) P by means of a rectangular region of interest (ROI) placed on a part of the cervical vein of the B-mode image. The reference direction setting circuit 25 averages the directions at all of the sampling volumes within the reference position (region) P to obtain an average direction. Then the average direction is sequentially sent to the reference direction storing/averaging circuit 26 so as to average over a certain period of time, thus calculating a reference direction D as a representative of the region P. The data of the reference direction D are sent to the code converting circuit 27 and color sample generating circuit 28.

The color sample generating circuit 28 outputs data of a color sample C in which a marker coincident with the calculated reference direction D is overlaid on given imaging colors. This color sample C is displayed on the color monitor 32, as shown in FIG. 8. In the color sample C, one main directional range of ±90 degrees whose center is the marker (i.e. reference direction D) is singly blue(BL) and the other main directional range of ±90 degrees which lies opposite to the marker (i.e. reference direction D) is singly red(RED). But a region of violet(VT) is shown on them, indicating poor detection accuracy. The marker enables the operator to readily recognize which way the reference direction is set during the scan or after recording images in photographs or VTRs.

The code converting circuit 27, as described above, is provided not only with the data of the reference direction D but also with the data of directions of blood flows at each sampling volume of a tomographic plane scanned from, the velocity/direction calculator 22. Therefore, in the circuit 27, as explained above, code data representing angular differences between the reference direction D and the calculated directions are created for every sampling volume. The code data are then sent, via the DSC 17, to the color converting circuit 29 for conversion into RGB video signals of corresponding imaging colors.

A white/black tomographic image presents a background and a blood flow image is displayed as shown in FIG. 8. Blood flow directions falling into one approximately half ring-like directional range including the reference direction are blue, blood flow directions falling into the other approximately half ring-like directional range opposite to the reference direction are red, and blood flow directions falling into a relatively narrow directional range of poor accuracy are violet.

Referring to the example of FIG. 8, a blood flow B1 (cervical vein) flowing down to the lower left side is blue, because its flowing direction is in conformity with the reference direction D, a blood flow B2 (carotid arteries) flowing up to the upper right side is red, because it is opposite to the reference direction D.

When applying the aforementioned conventional display technique (color imaging dependent on whether a blood flow is running toward a probe or not; the plus or minus sign of the velocity component) to FIG. 8, a blood flow B2a (branch of the carotid arteries) flowing down to the lower right side on the screen would be blue, because the flow of B2a is going away from the probe, although the flow B2a is the same stream as the flow B2. However according to the present embodiment, the branch B2a falls into the red half ring-like directional region, resulting in red, like other carotid arteries.

Such allowable directional range of ±90 degrees in judging the directions of blood flows properly prevents imaging colors of the blood flows flowing in the same direction from being changed on their way. And the blood flows having the same direction are displayed by the same color. Therefor, for superficial blood vessels, a recognition property is remarkably enhanced for the directions of their flows.

Figure 9:
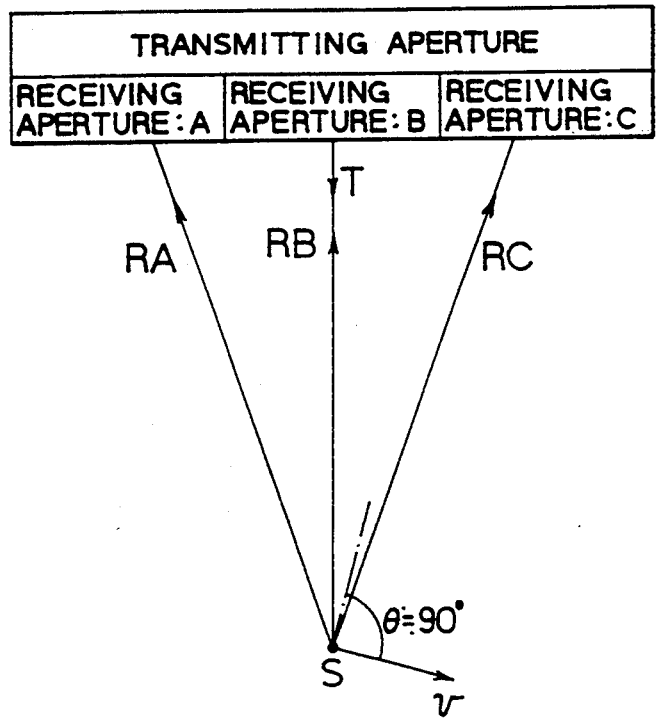
FIG. 9 is a variation of receiving ultrasonic beams.

Additionally, more than three receiving ultrasonic beams with highly accurate velocity detection can be provided. The velocity of a blood flow can be detected by two beams only. A plurality of pairs of two beams are formed when there are more than three beams. So, as shown in FIG. 9, when one pair RB and RC becomes almost perpendicular to a blood flow, an alternative pair RA and RB is not perpendicular to it. This means that proper exchange of pairs can eliminate the necessity of the aforementioned conversion code "99", i.e. imaging color of violet. Hence a color sample displayed is simplified and a measurable directional range is widened.

Further, although the above embodiment adopts the two main directional ranges of red and blue, the present invention is not limited to this. For example, each zone can be divided into a plurality of small ranges (i.e. directional ranges) which, have different hues, thus obtaining more precise direction display.

Still further, the above embodiment allows an operator to first input an arbitrary reference position through the input device 23. However, when superficial blood vessels are objects for diagnosis, the input device 23 can be preset to automatically specify a predetermined direction that is almost parallel rightward or leftward to the body surface on the monitor. This provides more simplified specification of the reference position.

A second embodiment will now be explained according to FIGS. 10 to 12. In this embodiment, the directions of blood flows at each sampling volume and their velocity magnitudes are displayed.

Figure 10:
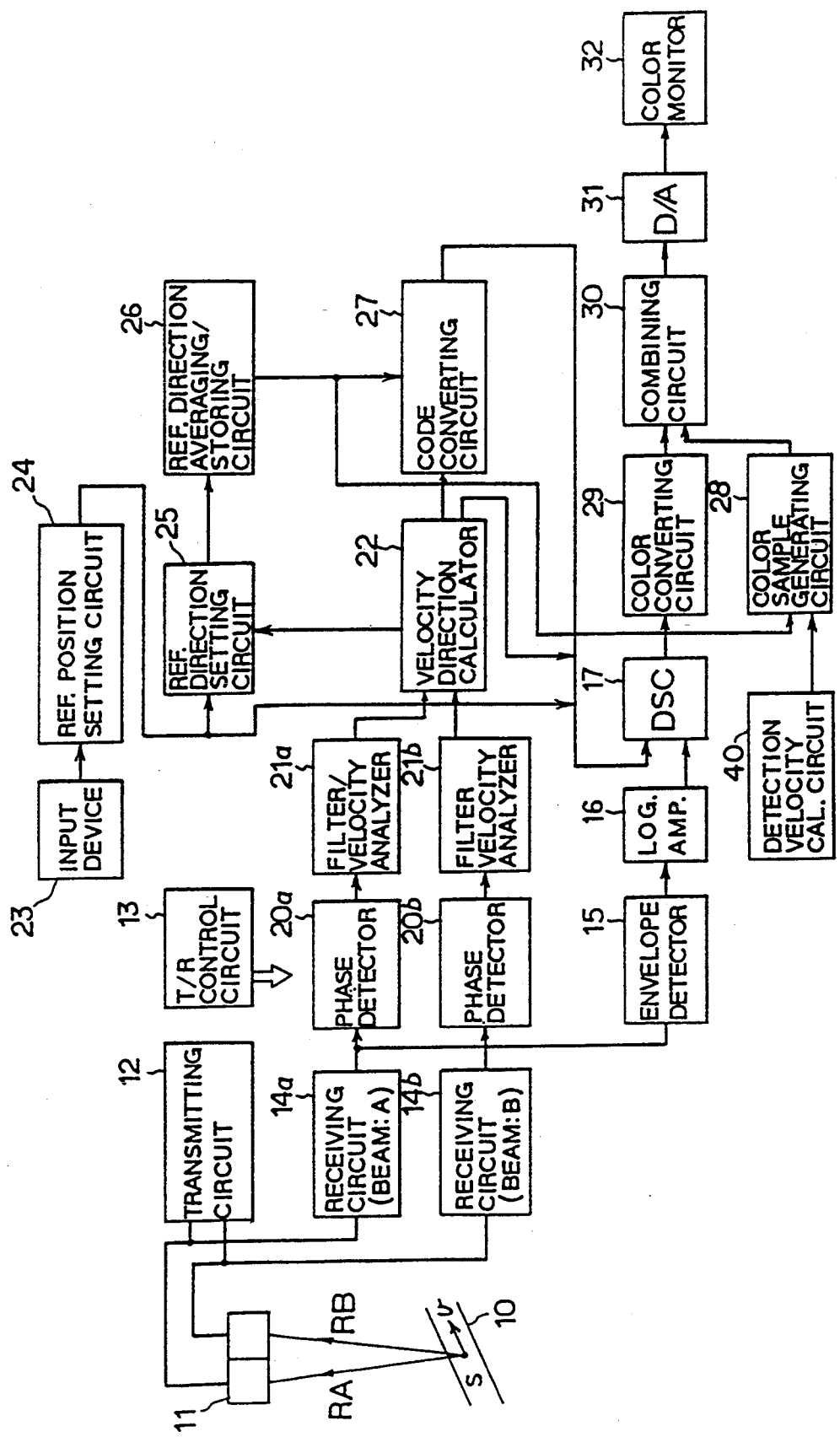
FIG. 10 shows in block form a second example of a color Doppler-type ultrasonic diagnostic apparatus according to the present invention.

A color Doppler-type ultrasonic diagnostic apparatus shown in FIG. 10 further comprises a detection velocity calculating circuit 20. This circuit 20 will calculate the detectable minimum and maximum velocities, in every direction $\theta$ of blood flows, for the direction of a given receiving ultrasonic beam, with the data of the velocities being supplied to the color sample generating circuit 28.

The detection velocity calculating circuit 40 calculates as follows. Assuming that, in FIG. 5, in view of FIG. 3, a blood flow direction is $\theta$ to a standard direction (e.g. the zero degree of the coordinate system designated), a beam direction is $\theta_0$ to the standard direction, and the Nyquist frequency for a frequency analysis is fmax, a detectable maximum velocity VmaxA at one aperture A is expressed as $$V_{maxA} = \frac{C \cdot f_{max}}{f_0 = \left[\cos(\theta - \theta_0) + \cos\left\{\theta - \theta_0 + \tan^{-1}\left(\frac{W}{4R}\right)\right\}\right]} \quad (5)$$

Also a detectable maximum velocity VmaxB at the other aperture B is expressed as $$V_{maxB} = \frac{C \cdot f_{max}}{f_0 = \left[\cos(\theta - \theta_0) + \cos\left\{\theta - \theta_0 + \tan^{-1}\left(\frac{W}{4R}\right)\right\}\right]} \quad (6)$$

A velocity Vmax, for which aliasing does not occur for both the apertures A and B, is either one of VmaxA or VmaxB, whichever is smaller than the other.

Figure 11A:
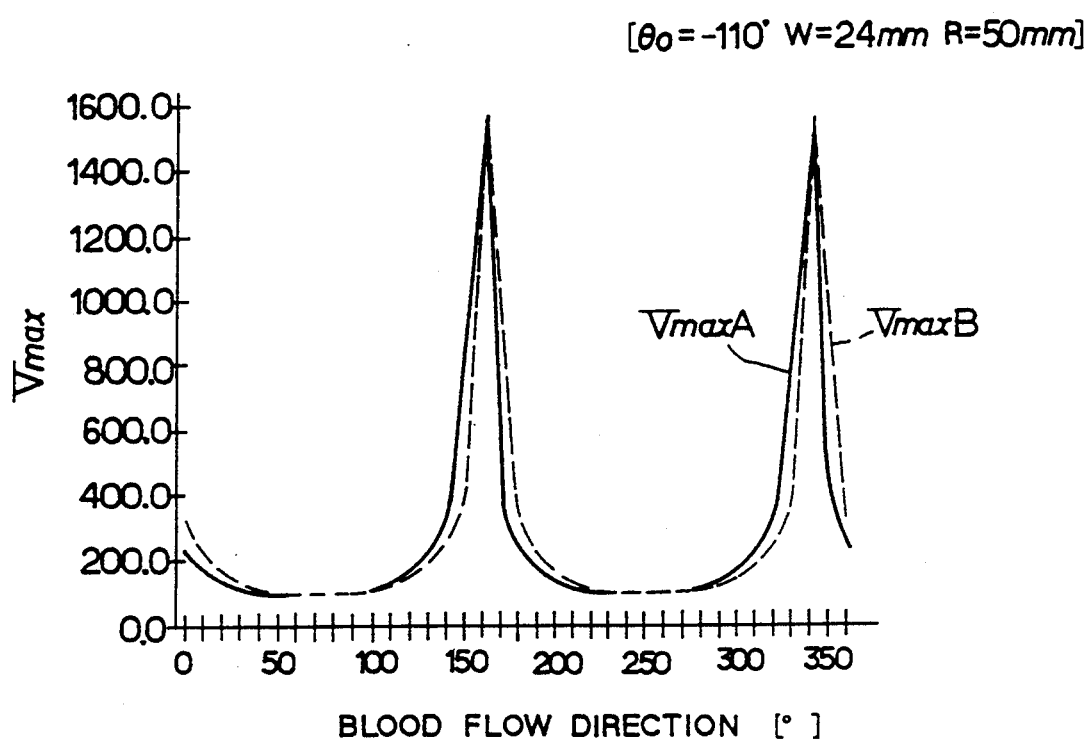
FIGS. 11A to 11C are graphs for explaining detectable maximum and minimum velocities.

The detectable maximum velocities VmaxA and VmaxB are shown as FIG. 11A. Using the values of FIG. 11A enables the magnitude of a maximum velocity Vmax in each direction $\theta$ to be shown as in FIG. 11B.

In order to calculate detectable minimum velocities VminA and VminB at both of the apertures A and B, the same calculation as the expressions (5) and (6) is applied by substituting VminA, VminB and fmin instead of VmaxA, VmaxB and fmax in those expressions.

Figure 11B:
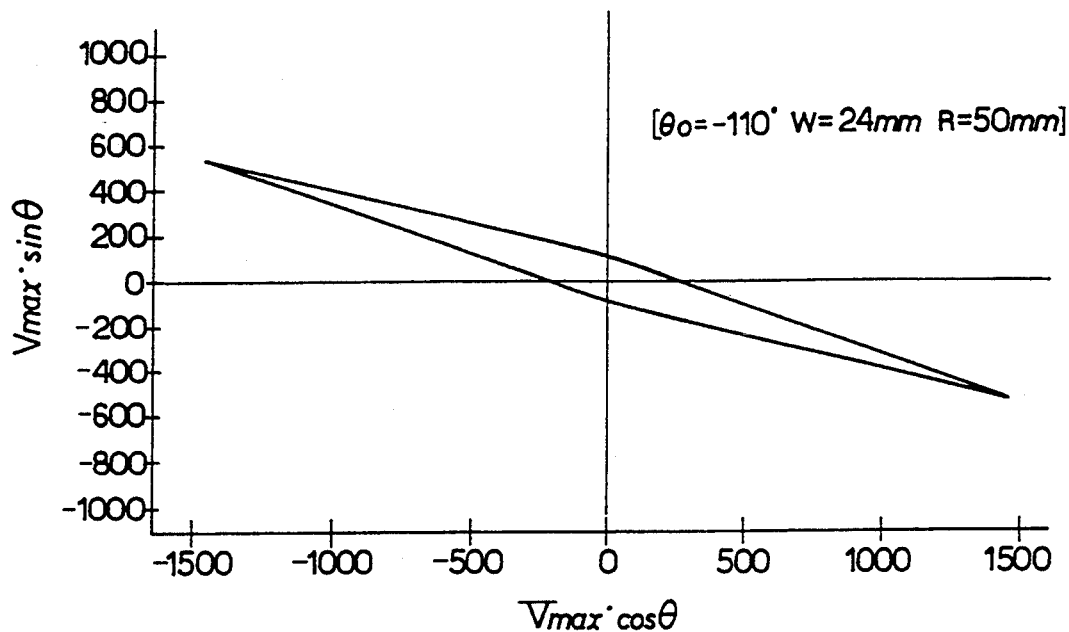
Figure 11C:
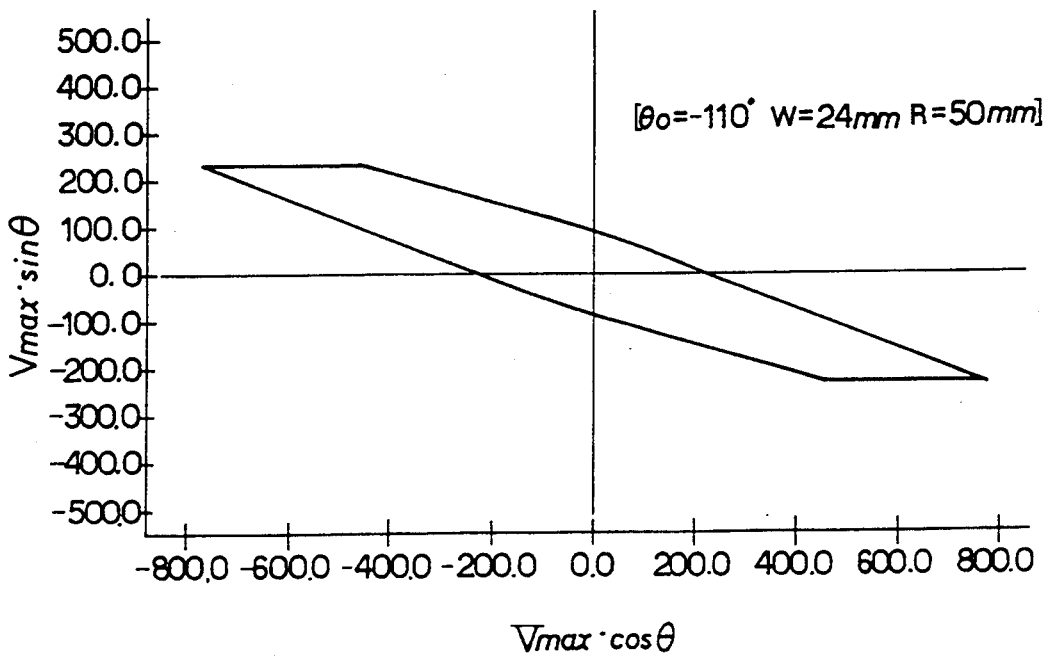
Figure 12:
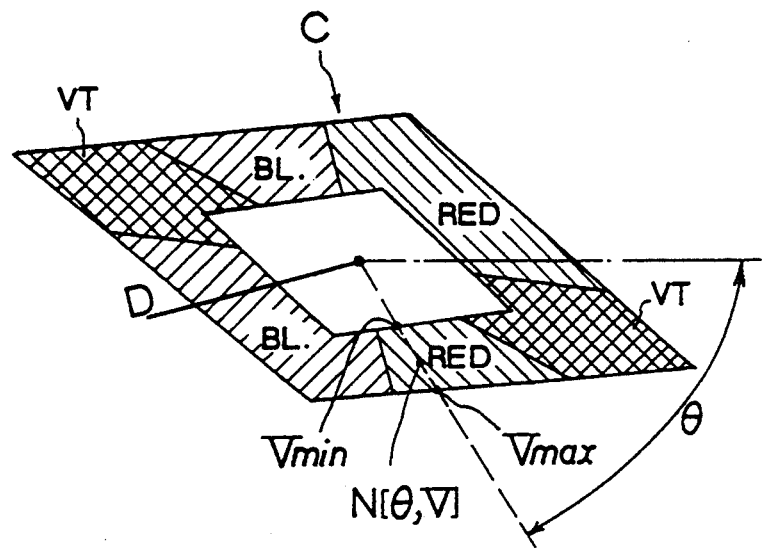
FIG. 12 shows a color sample in the second embodiment.

One color sample, therefore, can be shown as in FIG. 12, based on the values of FIG. 11B for Vmax and similarly calculated values for Vmin.

There is another way of obtaining the color sample. As to the detectable maximum velocity Vmax, the above simple calculation has produced the values of FIG. 11B, which is formed into a rhombus having a ratio of more than ten between its length and width. Angular ranges in which the magnitudes of Vmax are very large are poor in accuracy for velocity calculation, because the angle between a blood flow and ultrasonic beam directions is 90 degrees or approximately 90 degrees. Taking the angular ranges of poor accuracy into account, it is desirable to limit the displayed length of the longer diagonal of the rhombus.

The following is one example of a shortened diagonal. Each of the frequency spectrums for both of the apertures A and B is spread by an approximate $$Bf = 1 + \{(W/4R) \tan(\theta - \theta_0)\}.$$

In the frequency band in which the spectrum is larger than two times of the above value Bf, it is difficult to accurately calculate its center frequency. Two times the value Bf can be set as an upper limit of the diagonal, thus providing a deformed shape, shown in FIG. 11C, with the longer diagonal sliced in parallel to a zero line of "Vmax.sin $\theta$. Accordingly, a color sample having the shape in FIG. 11C can be adopted. Further, an ellipse close to the above deformed shape may also be used.

The generating circuit 2B shown in FIG. 10 forms data of a rhombus and ring-like color sample C, as shown in FIG. 12, on which data of a reference direction D specified by an operator like the first embodiment are overlaid simultaneously, the generating circuit 28 selects the inner and outer diameters of the color samples C of the proportionally corresponding lengths to show the detectable minimum and maximum velocities for every blood flow direction $\theta$, respectively. Moreover, data of the color samples C is gradually changed in brightness over the radial direction from the inner to outer diameters; for example, the brightness is changed from a lower to a higher degree.

The code converting circuit 27 will convert direction data of blood flows given from the velocity/direction calculator 22 into corresponding codes individually in the same way as the first embodiment. The converted direction data are then sent, via the DSC 17, to the color converting circuit 29, by which the direction data are converted into RGB video data like the first embodiment. The velocity magnitude data are converted into corresponding changed brightness data in the converting circuit 29.

In the color sample displayed in FIG. 12, an angle $\theta$ shows the direction of the velocity of a blood flow, a distance from the center shows the magnitude of its velocity, and in addition, the inner and outer diameters show the delectable minimum and maximum velocities Vmin and Vmax in a direction of an angle $\theta$ between the blood flow direction and beam direction. As for the shape of the color sample, when the receiving ultrasonic beam is more closely parallel to a blood flow (when $\theta$ becomes smaller), the detectable minimum and maximum velocity Vmin and Vmax (magnitude) is smaller; when the beam is more closely perpendicular to a blood flow (when $\theta$ becomes smaller), the velocities Vmin and Vmax (magnitude) are larger. Further, the directional ranges, which are displayed in violet, have deteriorating detection accuracy.

Therefore, the color sample C is capable of expressing both the direction and magnitude of a velocity of a blood flow through a displayed color and its brightness. For example, in FIG. 12, the blood flow at a sampling volume expressed by the color and brightness of a position N on the color sample C is readily understood to be the direction $\theta$ and magnitude V of the velocity. Thus, using this color sample C enables a color blood image to represent at the same time the direction and magnitude of a blood flow velocity for every sampling volume, resulting in simpler and more accurate analysis of blood flows.

In the above embodiment, the magnitude of a blood flow velocity (in other words, the distance from the center on the color sample) may be displayed by changed hues, instead of the changed degrees of brightness.

A third embodiment of the present invention will be explained according to FIG. 13, in which a display is more simplified than in the second embodiment. The hardware is equivalent to that in FIG. 10.

Figure 13:
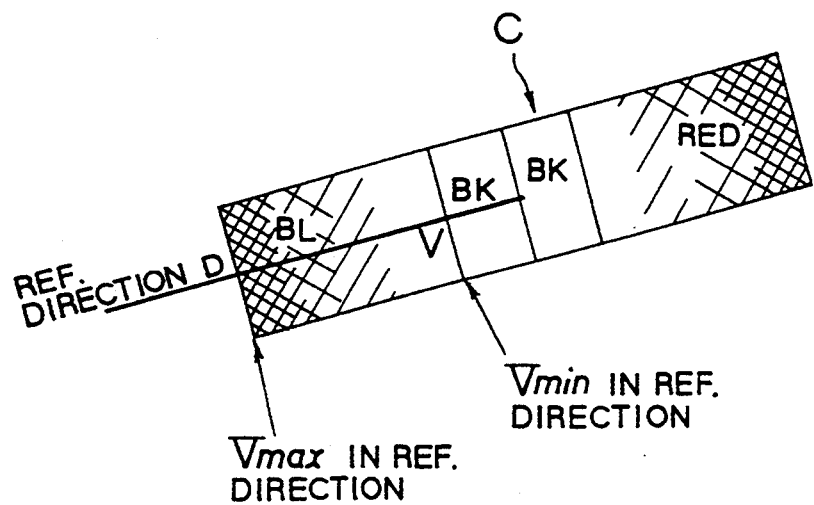
FIG. 13 shows a color sample in a third embodiment of the present invention.

A color sample, formed by the color sample generating circuit 28 of this embodiment, is stap-like as shown in FIG. 13. In the color sample C, a reference direction D is formed by a central axis extending from the center toward a longitudinal end. Thus the color sample is titled according to the angle of a specified reference direction D.

One directional range within ±90 degrees for the reference direction D centered therein is displayed by colors of blue or the like and the other directional range with ±90 degrees opposite to one range is displayed by colors of red or the like. The magnitudes of blood flow velocities are expressed by slight changes in hues. In conformity with this, the magnitudes are converted into corresponding changed hues.

In the color sample C, the detectable minimum velocity Vmin from the detection velocity calculating circuit 40 is expressed by boundaries between a central black region and the blue or the like region and between the central black region and the red or the like region. The detectable maximum velocity Vmax corresponds to each of the lengths from the longitudinal center to both of the color sample ends.

This simplified color sample can be used to easily recognize the directions of blood flows in comparison with a reference direction and to display the magnitudes of velocities with relatively high accuracy.

A fourth embodiment of the present invention will be described according to FIGS. 14 through 17A and 17B, in which blood flows will be displayed three-dimensionally. The hardware in this embodiment is equivalent to that in FIG. 10.

Figure 14:
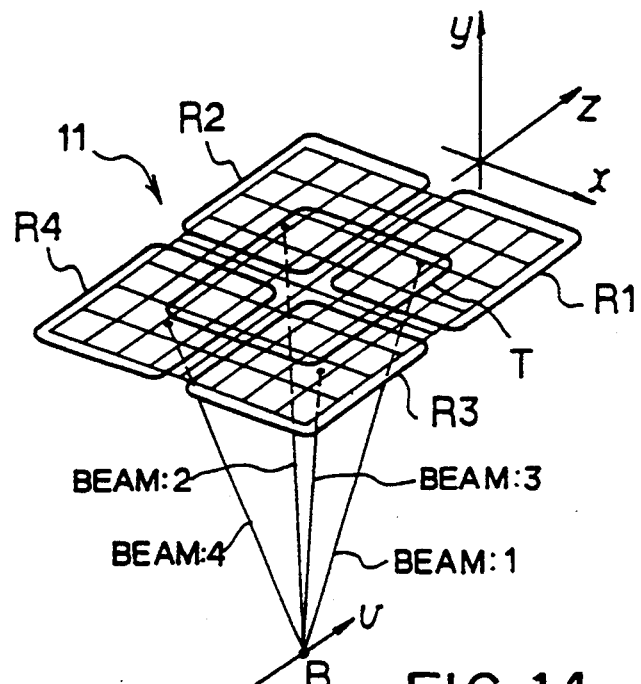
FIG. 14 is an illustration showing a probe aperture of a fourth embodiment of the present invention.
Figures 15A, 15B:
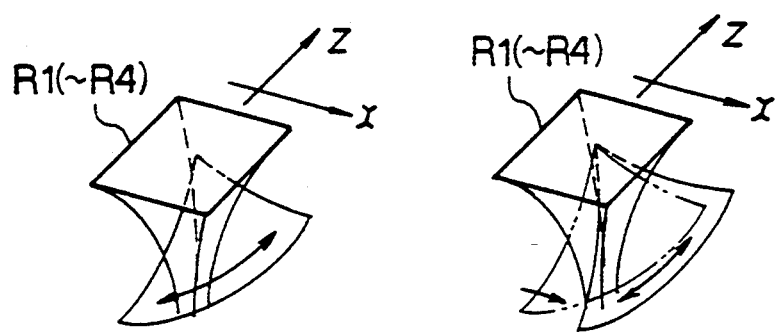
FIGS. 15A and 15B are illustrations for a three dimensional scanning.

The transducer 11 is formed into a two-dimensional matrix array shown in FIG. 14, thus forming four receiving ultrasonic beams for focusing, for instance, through receiving circuits.

A three-dimensional scanning using the above transducer 11 permits three-dimensional vectors of blood flow velocities to be obtained. In detail, a transmitting focus is made with a transmitting aperture T (refer to FIG. 14), and receiving focuses are made with four receiving apertures R1 to R4 (refer to FIG. 14). When receiving, each receiving ultrasonic beam of the apertures R1 to R4 is first scanned along the z-axis direction at a position in the x-axis direction (refer to FIG. 15A), to form a scanning plane across the x-axis. Then a scanning position is moved in the x-axis direction and the scanning is performed along the z-axis direction (refer to FIG. 15B). The same scanning, which will be repeated sequentially, allows all the beams of the apertures R1 to R4 to scan three-dimensionally, because the y-axis direction (i.e. depth from a body surface) is a time axis of echoed beams also scanned.

Figure 16A:
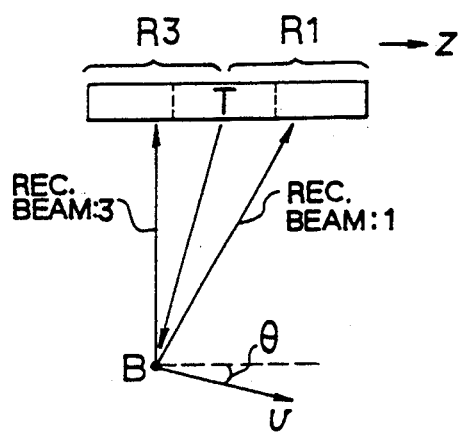
FIGS. 16A and 16B are illustrations for blood flow angles.
Figure 16B:
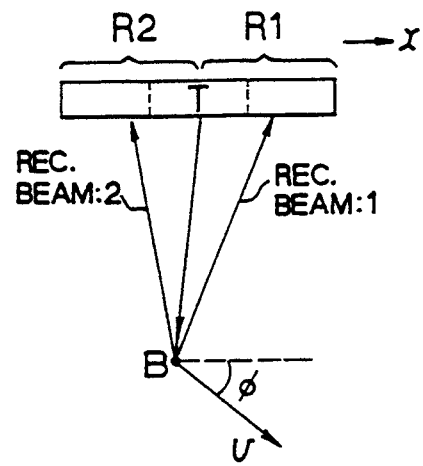

Thus, a blood flow B having a velocity magnitude v at a given sampling volume position can be specified three-dimensionally by a combination of angle $\theta$ in a first cross section scanned along the z-axis direction at the flow B as shown in FIG. 16A and an angle $\phi$ in a second cross section, normal to the first cross section, scanned along the x-axis direction at the flow B as shown in FIG. 16B.

The velocity/direction calculator 22 calculates not only the velocity magnitude v and angle $\theta$ for the first cross section but also the velocity magnitude v and angle $\phi$ for the second cross section. The angle $\theta$ can be calculated on the basis of a ratio between Doppler shift frequencies of the apertures R1 and R3 and a ratio between Doppler shift frequencies of the apertures R2 and R4. The angle $\phi$ can also be calculated on the basis of a ratio between Doppler shift frequencies of the apertures R1 and R2 and a ratio between Doppler shift frequencies of the apertures R3 and R4.

Further, for each of the first and second cross sections, the code converting circuit 27 and color converting circuit 29 operate individually to yield direction code data and the RGB video data, as described above. The reference direction setting circuit 25 generates two reference directions D1 and D2 specified for every cross section by an operator, which are sent to the color sample generating circuit 28.

Figure 17A:
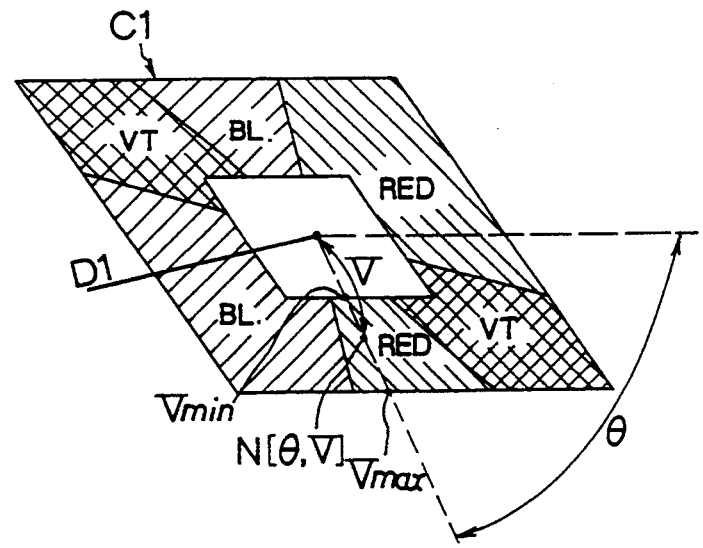
FIGS. 17A and 17B show the two color samples in the fourth embodiment.
Figure 17B:
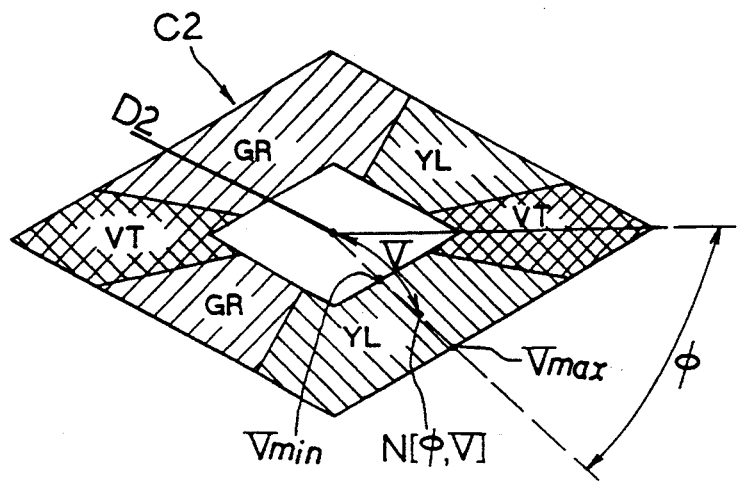

In the generating circuit 28, data of two color samples C1 and C2 are generated as shown in examples of FIGS. 17A and 17B. The first color sample C1 in FIG. 17A is for the angle $\theta$ in the first cross section and is the same as that in the above embodiments. In contrast, the second color sample C2 in FIG. 17B is for the angle $\phi$ in the second cross section. In the second color sample C2, a main directional range of predetermined angles including the reference direction D2 is displayed in green (GR) and a main directional range of predetermined angles including the opposite direction to the reference direction D2 is displayed in yellow (YL). The first and second color samples C1 and C2 are each displayed together with color blood images of the first and second cross sections on the color monitor 32.

This enables easier and accurate handling of three-dimensional display of blood flows.

Figure 18:
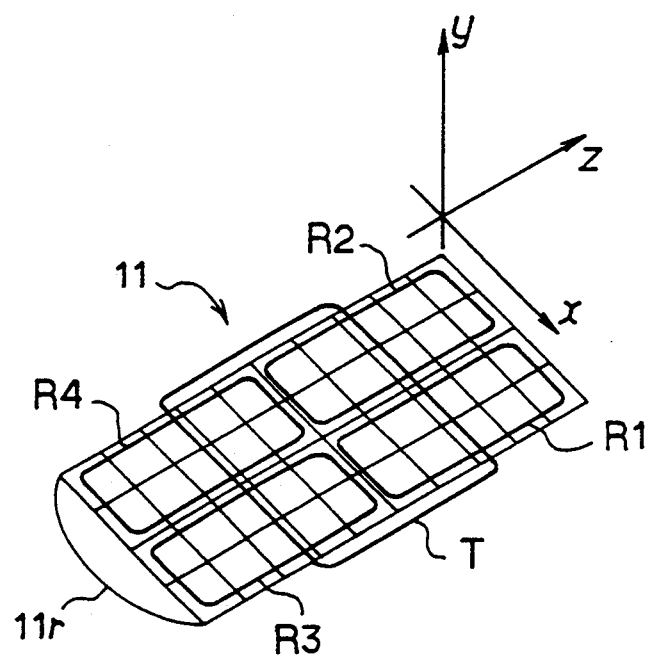
FIG. 18 is a variation of the probe aperture in the fourth embodiment.

Additionally, a two-dimensional array-type piezoelectric transducer, which scans in its scanning direction (z-direction) and changes receiving apertures in its lens direction (x-direction), can also be used to detect a flow velocity. FIG. 18 represents an example of the divided form for the apertures of this type of transducer; namely, the linear array-type transducer is divided into pluralities in its lens direction to change the apertures. In FIG. 18, the reference numerals are the same as in FIG. 14 and reference 11r shows an acoustic lens. In this exemplified structure, a transmitting aperture T is used for a transmitting focus and receiving apertures R1 to R4 are each used for receiving focuses. The beams can be scanned only along the z-direction and cannot be scanned along the x-direction; only tomographic images in the z-direction are obtained. Three-dimensional vectors of blood flows are obtained and displayed in the same manner as described above.

A fifth embodiment of the present invention will be explained with FIGS. 19 and 20. This embodiment is applied to scan methods such as a sector scan and convex scan, in which the angle of a receiving ultrasonic beam varies depending on its scanning position.

Figure 19:
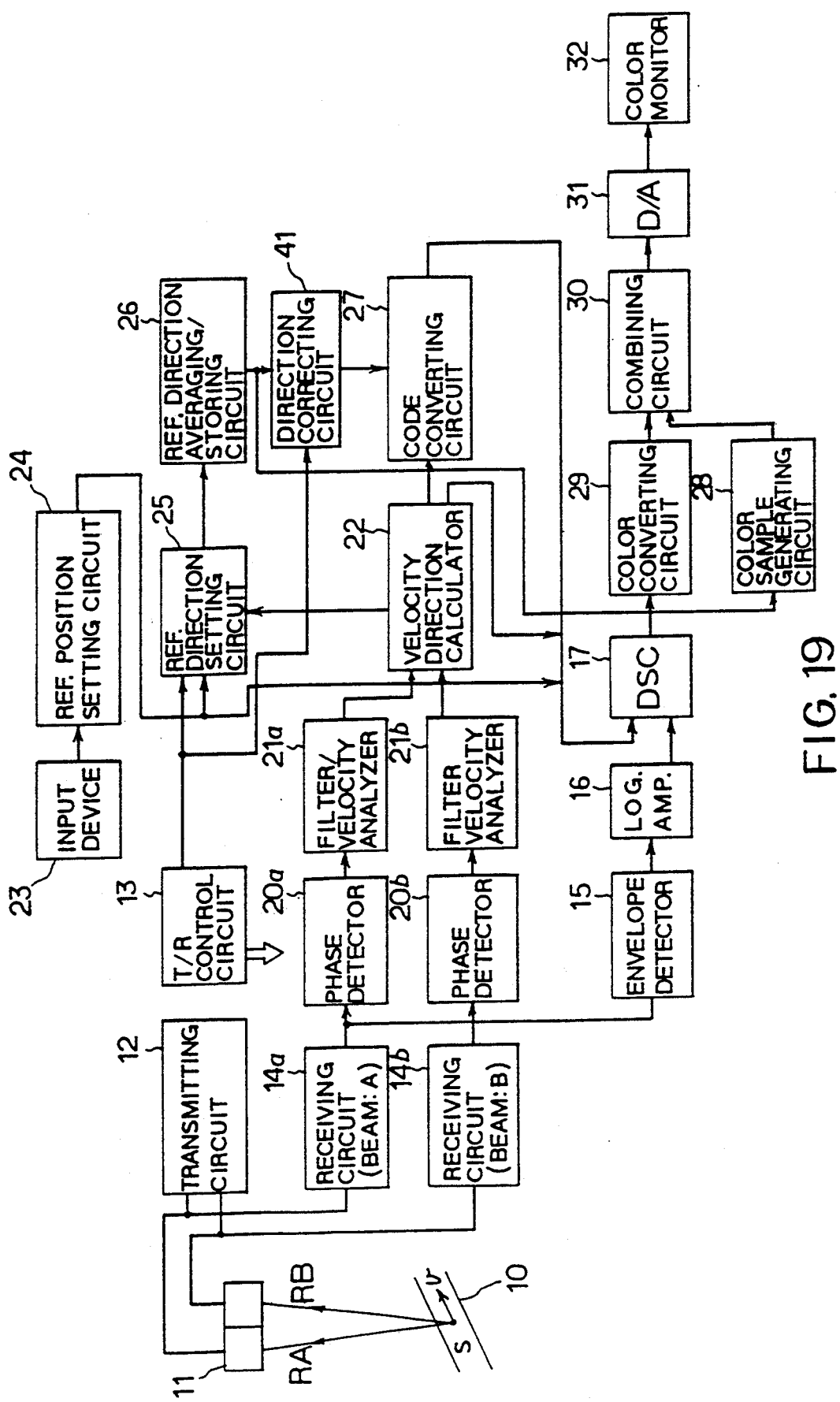
FIG. 19 shows in block form a fifth example of a color Doppler-type ultrasonic diagnostic apparatus according to the present invention.

A color Doppler-type ultrasonic diagnostic apparatus shown in FIG. 19 adopts an electronic sector scanning method. In addition to the construction of FIG. 2, the apparatus comprises a mechanism for correcting a reference direction depending on the scanning angle of a receiving ultrasonic beam. The reference direction setting circuit 25 receives from the transmitting/receiving control circuit 13, a signal representing the angle that the receiving ultrasonic beam takes against the transducer 11 at a reference position specified.

Accordingly, the reference direction setting circuit 25 not only calculates a blood flow direction (reference direction) at the reference position but also corrects the calculated reference direction with regard to a predetermined direction on the basis of the received angle signal from the transmitting/receiving control circuit 13. The corrected reference direction is averaged in the reference direction storing/averaging circuit 26, and sent to a direction correction circuit 41 and color sample generating circuit 28.

From the transmitting/receiving control circuit 13, the direction correcting circuit 41 will receive a signal representing an angle relationship between the transducer 11 and the receiving ultrasonic beam direction, the angle relationship varying every moment due to the scanning directions. In the correction circuit 41, the reference direction is corrected, depending on the angular position of a presently activated scanning line. The corrected reference direction is then sent to the code converting circuit 27 and used for judging the angular difference between the momentarily given reference direction and the blood flow direction for every sampling volume, in the same manner as in the first embodiment.

Figure 20:
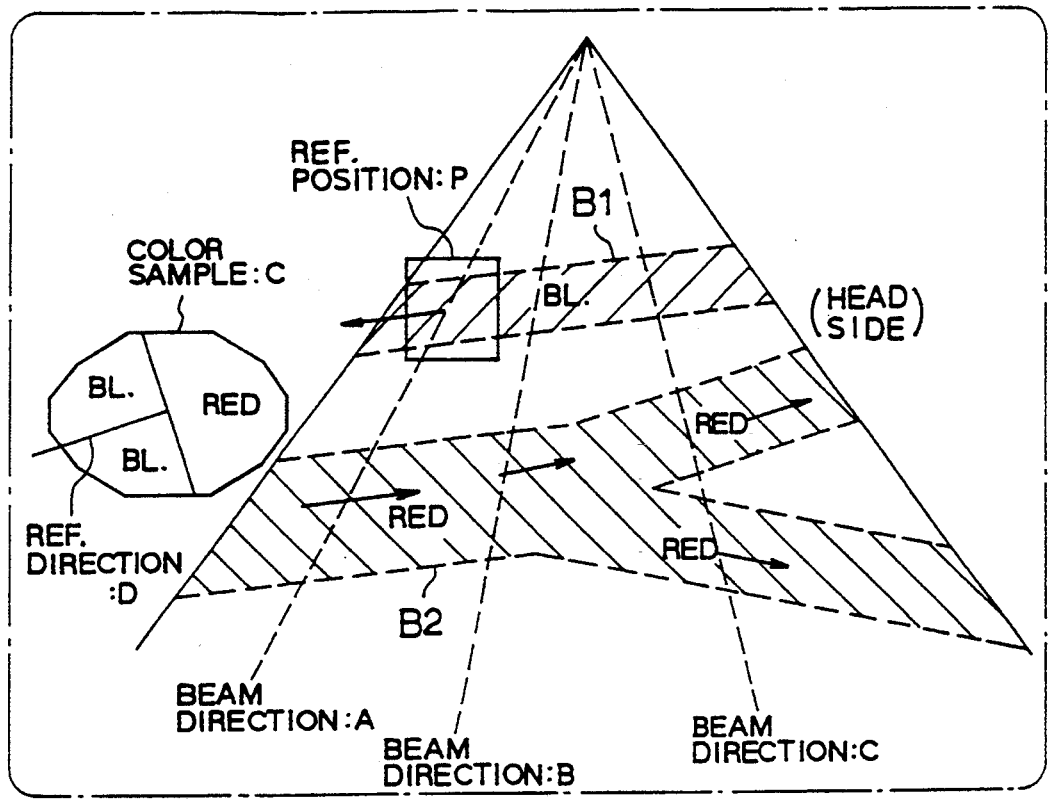
FIG. 20 is an example of a displayed image for a sector scan according to the fifth embodiment.

The color sample generating circuit 28 forms an approximately ellipsoidal color sample C shown in FIG. 20, on which the reference direction is fixedly overlaid such that it is not concerned with the angles of the receiving ultrasonic beams (scanning lines). In this color sample C, directions are shown only by colors; blue is one directional range of ±90 degrees whose center is the reference direction D and red is the other directional range of ±90 degrees opposite to it. This color sample C is displayed fixedly (i.e. not changed by the scanning) on the color monitor 32, as shown in FIG. 20, together with a color blood image by the electronic sector scanning.

Thus, even if a scanning method is used where the receiving beam direction is changed every scanning line, by momentarily correcting the angle of the reference direction D and setting directional ranges showing whether or not the blood flow is along the reference direction D, it is possible to properly display blood flow directions as one of the parameters for blood flow movement. This avoids the drawback that the same blood vessel is imaged in changed colors along the way. For this sector scanning, it is difficult to display the aforementioned region of poor detection accuracy and detectable minimum and maximum velocities for every detecting direction, but processing load is accordingly reduced.

Figure 21:
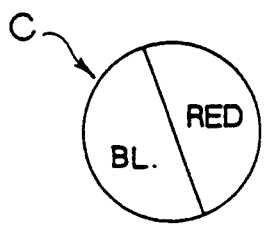
FIGS. 21 and 22 are each another color sample adoptable into the fifth embodiment.
Figure 22:
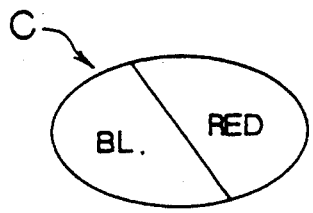

For the color sample in the fifth embodiment, it is possible instead to deform it into a circular shape shown in FIG. 21 or an ellipse shape shown in FIG. 22, for example.

Further, for the above embodiments in which hues are used as color information representing blood flow directions, it is possible to adopt degrees of color saturation and changes in brightness, instead of hues.

Still further, the method of calculation for the directions and magnitudes of flood flow velocities (absolute velocities) is not limited to the described methods. For example, the velocities can be calculated according to differences in velocity between adjacent sampling volumes.

Furthermore, a moving target of the present invention is not limited to a blood flow, and may adopt, for example, a urine flow in the bladder and a humor flow in the cerebral vesicle. Also, the cardiac muscle of a heart that periodically moves in an object being examined may be also included in the moving target.

What I claim is:

1. A color Doppler-type ultrasonic diagnostic apparatus having an ultrasonic pulse beam transmitted from a transducer of a transmitting means along a cross section to be scanned toward an object being examined and containing a moving target therein, a Doppler shift frequency detected on the basis of the ultrasonic pulse beam echoed from the moving target and received by a receiving means for one of a plurality of sampling points of the cross section, and a tomographic image of the cross section displayed on a monitor, the apparatus comprising:

means for calculating movement information including a direction and a magnitude of velocity of the moving target for each of the sampling points on the basis of the detected Doppler shift frequency;

means for specifying a reference direction on the tomographic image of the cross section;

means for forming data of a color sample showing a directional relation between the calculated direction and the specified reference direction;

means for creating two-dimensional color display data of the calculated velocities at the plurality of sampling points on the basis of the directional relation; and means for color-displaying at least the created two-dimensional color display data together with the formed data of the color sample.

2. A color Doppler-type ultrasonic diagnostic apparatus according to claim 1, wherein the moving target is a flow of blood.

3. A color Doppler-type ultrasonic diagnostic apparatus according to claim 1, wherein the reference direction specifying means specifies the reference direction parallel to a transmitting and receiving surface of the transducer.

4. A color Doppler-type ultrasonic diagnostic apparatus according to claim 1, wherein each of the transmitting and receiving means includes means for performing an electronic linear scan such that a plurality of scanning lines parallel to each other are formed by the transmitted and received pulse beams.

5. A color Doppler-type ultrasonic diagnostic apparatus according to claim 4, wherein the reference direction specifying means comprises:

means for pointing to a desired reference position on the tomographic image; and means for setting the reference direction at the reference position by using a calculated direction at the reference position.

6. A color Doppler-type ultrasonic diagnostic apparatus according to claim 5, wherein the reference position is formed by a single point on the tomographic image.

7. A color Doppler-type ultrasonic diagnostic apparatus according to claim 5, wherein the reference position is formed by a region having an area containing a portion of the plurality of sampling points on the tomographic image.

8. A color Doppler-type ultrasonic diagnostic apparatus according to claim 7, wherein the reference direction setting means has means for calculating an averaged direction for the portion of the plurality of sampling points within the region using the direction calculated by the movement information calculating means.

9. A color Doppler-type ultrasonic diagnostic apparatus according to claim 5, wherein the directional relation includes binary information indicating the calculated direction is either one of a direction approximately oriented along the reference direction and a direction approximately opposed to the reference direction.

10. A color Doppler-type ultrasonic diagnostic apparatus according to claim 9, wherein the binary information is formed by information of two main directional ranges arranged in the color sample, a first main directional range being less than 90 degrees and having the reference direction centered in the first main directional range and a second main directional range being less than ±90 degrees and having a direction being opposite to the reference direction and being centered in the second main directional range.

11. A color Doppler-type ultrasonic diagnostic apparatus according to claim 10, wherein the color display data creating means has means for classifying each of the calculated directions at the plurality of sampling points into the two main directional ranges.

12. A color Doppler-type ultrasonic diagnostic apparatus according to claim 11, wherein the color sample data forming means includes means for identifying the two main directional ranges with different colors.

13. The color Doppler-type ultrasonic diagnostic apparatus according to claim 12, wherein the identifying means identifies the first main directional range with blue and the like and identifies the second main directional range with red and the like.

14. A color Doppler-type ultrasonic diagnostic apparatus according to claim 11, wherein the color sample data forming means has means for shaping the color sample into either one of a circle, an ellipsoid and a ring.

15. A color Doppler-type ultrasonic diagnostic apparatus according to claim 11, wherein the color sample data forming means has means for overlaying a marker data showing a directional position of the reference direction onto the data of the color sample.

16. A color Doppler-type ultrasonic diagnostic apparatus according to claim 15, wherein the marker data is formed by a data of either one of a line and an arrow.

17. A color Doppler-type ultrasonic diagnostic apparatus according to claim 10, wherein the color sample data forming means has means for shaping the color sample into a ring.

18. A color Doppler-type ultrasonic diagnostic apparatus according to claim 17, wherein the color sample data forming means has means for overlaying a marker data showing a directional position of the reference direction onto the color sample.

19. A color Doppler-type ultrasonic diagnostic apparatus according to claim 18, wherein the color sample data forming means has means for expressing the magnitude of the velocity by a radial distance from a ring center of the color sample, the radial distance being positioned at an angle in accordance with the direction of the velocity, and means for changing color data in each of the radial directions of the color sample.

20. A color Doppler-type ultrasonic diagnostic apparatus according to claim 19, wherein the means for changing color data changes the degree of brightness of the color.

21. A color Doppler-type ultrasonic diagnostic apparatus according to claim 19, further comprises means for calculating detectable maximum and minimum velocities of the moving target, the detectable maximum and minimum velocities depending on a scanning direction of the echoed ultrasonic pulse beam, wherein the color sample data forming means has means for limiting data of outer and inner diameters of the color sample in accordance with the calculated detectable maximum and minimum velocities, respectively.

22. A color Doppler-type ultrasonic diagnostic apparatus according to claim 17, wherein the directional relation of the color sample data forming means includes information showing the calculated direction falling in an auxiliary directional range less than a directional angular range of ±90 degrees having an angular center direction perpendicular to the echoed ultrasonic pulse beam.

23. A color Doppler-type ultrasonic diagnostic apparatus according to claim 22, wherein the color sample data forming means has means for giving the auxiliary directional range color data different from the color data of the two main directional ranges.

24. A color Doppler-type ultrasonic diagnostic apparatus according to claim 17, wherein the color sample data forming means has means for shaping the color sample into a rectangle having a longitudinal direction.

25. A color Doppler-type ultrasonic diagnostic apparatus according to claim 24, wherein the color sample data forming means has means for placing the two main directional ranges on two longitudinal outward side portions of the rectangle, the two portions separated in the longitudinal direction from each other by a center portion having a longitudinal center of the rectangle.

26. A color Doppler-type ultrasonic diagnostic apparatus according to claim 25, wherein the color sample data forming means has means for overlaying a marker data showing a directional position of the reference direction onto the data of the color sample, the marker data arranged from the longitudinal center of the rectangle toward one longitudinal end of the rectangle.

27. A color Doppler-type ultrasonic diagnostic apparatus according to claim 26, further comprises means for calculating detectable maximum and minimum velocities of the moving target, the detectable maximum and minimum velocities depending on a scanning direction of the echoed ultrasonic pulse beam, wherein the color sample data forming means has means for limiting the longitudinal distance from the longitudinal center of rectangle to the outer and inner ends of each of the two side portions of the color sample in accordance with the calculated detectable maximum and minimum velocities, respectively.

28. A color Doppler-type ultrasonic diagnostic apparatus according to claim 27, wherein the color sample data forming means has means for expressing the magnitude of the velocity by a longitudinal distance from the longitudinal center of the color sample and means for changing color data of the color sample according to positions in the longitudinal direction of the color sample.

29. A color Doppler-type ultrasonic diagnostic apparatus according to claim 28, wherein the color data changing means changes hue data.

30. A color Doppler-type ultrasonic diagnostic apparatus according to claim 4, wherein the cross section to be scanned consists of two cross sections crossing each other in the object, each tomographic image of the two cross sections is displayed on the monitor, and the specifying means has means for specifying the reference direction on each of the tomographic images of the two cross sections.

31. A color Doppler-type ultrasonic diagnostic apparatus according to claim 30, wherein the transducer is a two-dimensional phased array-type transducer 32. A color Doppler-type ultrasonic diagnostic apparatus according to claim 31, wherein the two cross sections are perpendicular to each other.

33. A color Doppler-type ultrasonic diagnostic apparatus according to claim 32, wherein the color sample data forming means has means for producing two kinds of color samples each corresponding to one of the two tomographic images of the two cross sections and means for coloring the two color samples with different colors defined by the directional relation.

34. A color Doppler-type ultrasonic diagnostic apparatus according to claim 33, wherein the color-displaying means displays the created two-dimensional color display data for the two cross sections together with the formed data of the two color samples, respectively.

35. A color Doppler-type ultrasonic diagnostic apparatus according to claim 1, wherein the color-displaying means has a means for overlaying the created color display data of the moving target on the tomograhic image.

36. A color Doppler-type ultrasonic diagnostic apparatus according to claim 1, wherein each of the transmitting and receiving means includes means for performing an electronic scanning in which a scanning angle of the ultrasonic pulse beam is changed over its scan by which a plurality of scanning lines having changed scanning angles are formed by the transmitted and received pulse beam.

37. A color Doppler-type ultrasonic diagnostic apparatus according to claim 36, wherein the reference direction specifying means comprises:
means for pointing to a desired reference position on the tomographic image;
means for setting the reference direction at the reference position by using a calculated velocity direction at the reference position; and
means for correcting the reference direction in conformity with the changed scanning angle of the scanning lines.

38. A color Doppler-type ultrasonic diagnostic apparatus according to claim 37, wherein the reference position is formed by a region having an area containing a portion of the plurality of sampling points on the tomograhic image.

39. A color Doppler-type ultrasonic diagnostic apparatus according to claim 38, wherein the reference direction setting means has means for calculating an averaged direction over the portion of the plurality of sampling points within the region using the direction calculated by the movement information calculating means.

40. A color Doppler-type ultrasonic diagnostic apparatus according to claim 39, wherein the directional relation includes binary information indicating the calculated direction is either one of a direction approximately oriented along the reference direction and a direction approximately opposed to the reference direction.

41. A color Doppler-type ultrasonic diagnostic apparatus according to claim 40, wherein the binary information is formed by information of two main directional ranges arranged in the color sample, a first main directional range being less than ±90 degrees and having the reference direction centered in the first main directional range and a second main directional range being less than ±90 degrees and having a direction being opposite to the reference direction and being centered in the second main directional range.

42. A color Doppler-type ultrasonic diagnostic apparatus according to claim 41, wherein the color display data creating means has means for classifying each of the calculated directions at the plurality of sampling points into the two main directional ranges.

43. A color Doppler-type ultrasonic diagnostic apparatus according to claim 41, wherein the color sample data forming means includes means for identifying the two main directional ranges with different colors.

44. A color Doppler-type ultrasonic diagnostic apparatus according to claim 43, wherein the color sample data forming means has means for shaping the color sample into either one of a circle and an ellipsoid.

45. A color Doppler-type ultrasonic diagnostic apparatus according to claim 44, wherein the color sample data forming means has means for overlaying a marker data showing a directional position of the reference direction onto the color sample.

46. A color Doppler-type ultrasonic diagnostic apparatus according to claim 1, wherein the moving target is a cardiac muscle of a heart.

47. A color Doppler-type ultrasonic diagnostic apparatus according to claim 1, wherein the color sample data forming means has means for overlaying a marker data showing a directional position of the reference direction onto the color sample.

* * * * *

UNITED STATES PATENT AND TRADEMARK OFFICE
CERTIFICATE OF CORRECTION

PATENT NO. : 5,441,052
DATED : August 15, 1995
INVENTOR(S) : Yasuo MIYAJIMA

It is certified that error appears in the above-indentified patent and that said Letters Patent is hereby corrected as shown below:

Column 11, in formulas (5) and (6), at approximately line 18 and 27, after "fo", change the symbol "=" to --.--.

Column 11, in formula (6) at approximately line 27 after "$\theta_o$" (second occurrence), change the symbol "+" to -- - --.

Column 11, line 61, change "$\theta$O" to --$\theta_o$--.

Column 12, line 1, change " "Vmax.sin$\theta$" to --"Vmax sin$\theta$"--.

Signed and Sealed this

Eighteenth Day of June, 1996

Attest:

BRUCE LEHMAN

*Attesting Officer*   *Commissioner of Patents and Trademarks*